(12) United States Patent
Chen

(10) Patent No.: US 8,048,107 B2
(45) Date of Patent: Nov. 1, 2011

(54) FORCEPS

(75) Inventor: Cheng-Chi Chen, Taipei Hsien (TW)

(73) Assignee: Hon Hai Precision Industry Co., Ltd., Tu-Cheng, New Taipei (TW)

( * ) Notice: Subject to any disclaimer, the term of this patent is extended or adjusted under 35 U.S.C. 154(b) by 265 days.

(21) Appl. No.: 12/564,876

(22) Filed: Sep. 22, 2009

(65) Prior Publication Data

US 2011/0054509 A1    Mar. 3, 2011

(30) Foreign Application Priority Data

Aug. 31, 2009  (CN) .......................... 2009 1 0306404

(51) Int. Cl.
*A61B 17/50* (2006.01)
*B25B 7/00* (2006.01)
(52) U.S. Cl. ....................................... 606/210; 294/99.2
(58) Field of Classification Search .................. None
See application file for complete search history.

(56) References Cited

U.S. PATENT DOCUMENTS

| | | | | | |
|---|---|---|---|---|---|
| 1,758,490 | A | * | 5/1930 | Aderer | 294/99.2 |
| 2,764,905 | A | * | 10/1956 | Thoms | 294/99.2 |
| 3,818,784 | A | * | 6/1974 | McClure | 294/99.2 |
| 4,389,912 | A | * | 6/1983 | Dallons et al. | 81/320 |
| 4,452,106 | A | * | 6/1984 | Tartaglia | 294/99.2 |
| 4,761,028 | A | * | 8/1988 | Dulebohn | 294/99.2 |
| 4,938,214 | A | * | 7/1990 | Specht et al. | 606/174 |
| 5,899,513 | A | * | 5/1999 | Grisoni | 294/99.2 |
| 2008/0200914 | A1 | * | 8/2008 | Hanlon et al. | 606/48 |
| 2008/0312669 | A1 | * | 12/2008 | Vries et al. | 606/148 |
| 2011/0046620 | A1 | * | 2/2011 | Lewandowski et al. | 606/41 |

FOREIGN PATENT DOCUMENTS

| WO | WO2008071750 | * | 6/2008 |
|---|---|---|---|
| WO | WO2010108900 | * | 9/2010 |

* cited by examiner

*Primary Examiner* — Gary Jackson
*Assistant Examiner* — Amy Shipley
(74) *Attorney, Agent, or Firm* — Altis Law Group, Inc.

(57) ABSTRACT

A forceps includes two arms, two nipping tips and two sleeves. Each sleeve defines a through hole therein and forms a plurality of threads on an inner surface thereof. Each arm forms a first mounting pole towards a corresponding nipping tip. Each nipping tip forms a second mounting pole towards a corresponding arm. The first and second mounting poles each have a thread section and a smooth section. The first mounting pole and the second mounting pole abut against each other and are received in the through hole of a corresponding sleeve. The thread section of the first mounting pole and the thread section of the second mounting pole cooperatively form a thread pole. The smooth section of the first mounting pole and the smooth section of the second mounting pole cooperatively form a smooth pole. The sleeve is threaded with the thread pole.

8 Claims, 4 Drawing Sheets

FORCEPS

BACKGROUND

1. Technical Field

The disclosure generally relates to forceps, and particularly to a forceps which is reusable in that the nipping tips thereof are replaceable.

2. Description of Related Art

Forceps are common tools in our everyday life. A typical forceps is approximately V-shaped. The forceps includes two strip-shaped resilient arms. Top ends of the two resilient arms are joined together, and bottom ends of the two resilient arms are spaced from each other to form two nipping tips thereat. The nipping tips are configured for nipping objects which users desire. Each of the nipping tips is integrally formed with a corresponding resilient arm. When the nipping tips of a forceps are damaged, the forceps is discarded as a whole for that the nipping tips can not be replaced with new ones, which causes a considerable waste of resources.

For the foregoing reason, a forceps which can overcome the above described shortcoming is desired.

BRIEF DESCRIPTION OF THE DRAWINGS

Many aspects of the embodiments can be better understood with reference to the following drawings. The components in the drawings are not necessarily drawn to scale, the emphasis instead being placed upon clearly illustrating the principles of the present disclosure. Moreover, in the drawings, like reference numerals designate corresponding parts throughout the several views.

DETAILED DESCRIPTION

Figure 1:
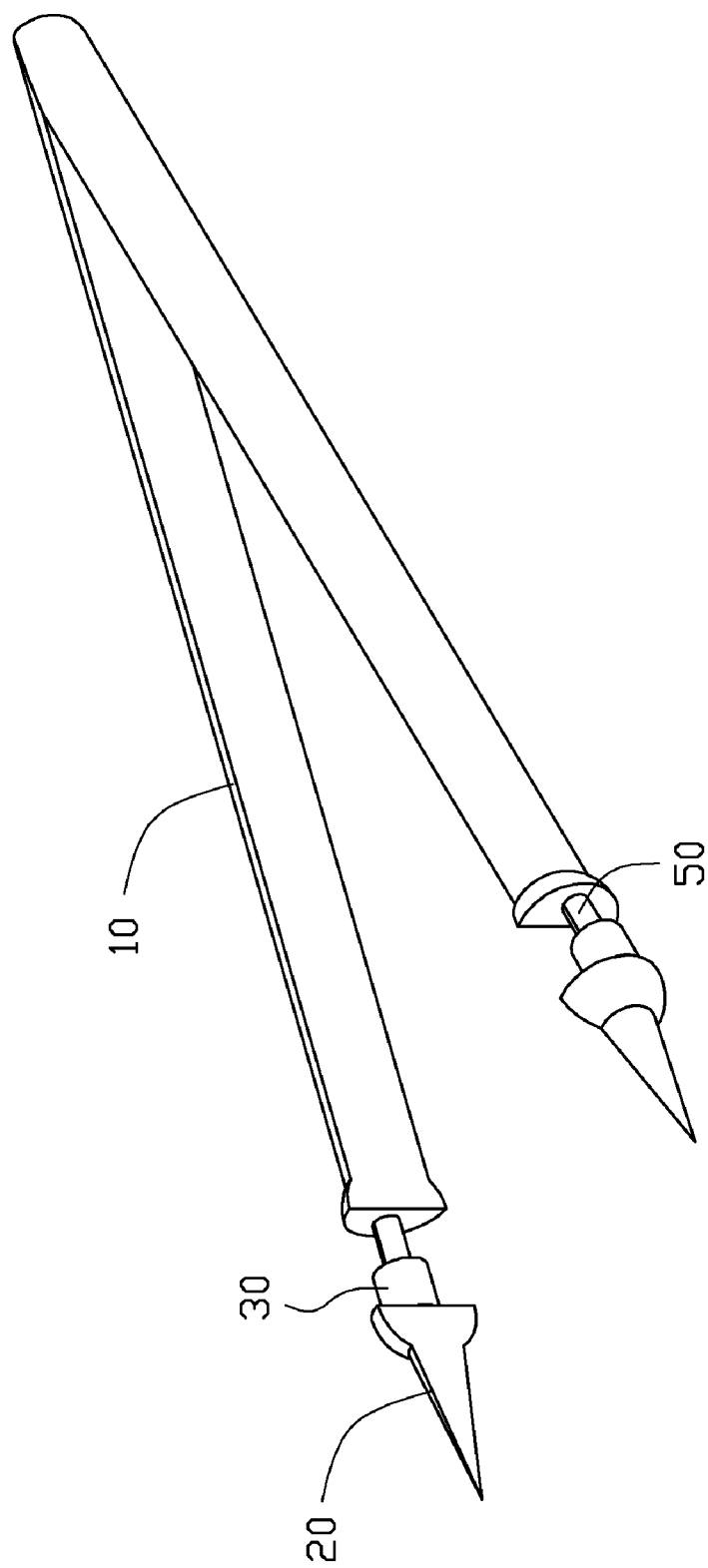
FIG. 1 is an isometric, assembled view of a forceps in accordance with an exemplary embodiment of the present disclosure.

Referring to FIG. 1, a forceps according to an embodiment of the present disclosure is shown. The forceps includes two arms 10, two nipping tips 20 and two sleeves 30 for respectively securing the two nipping tips 20 on the two arms 10.

Figure 2:
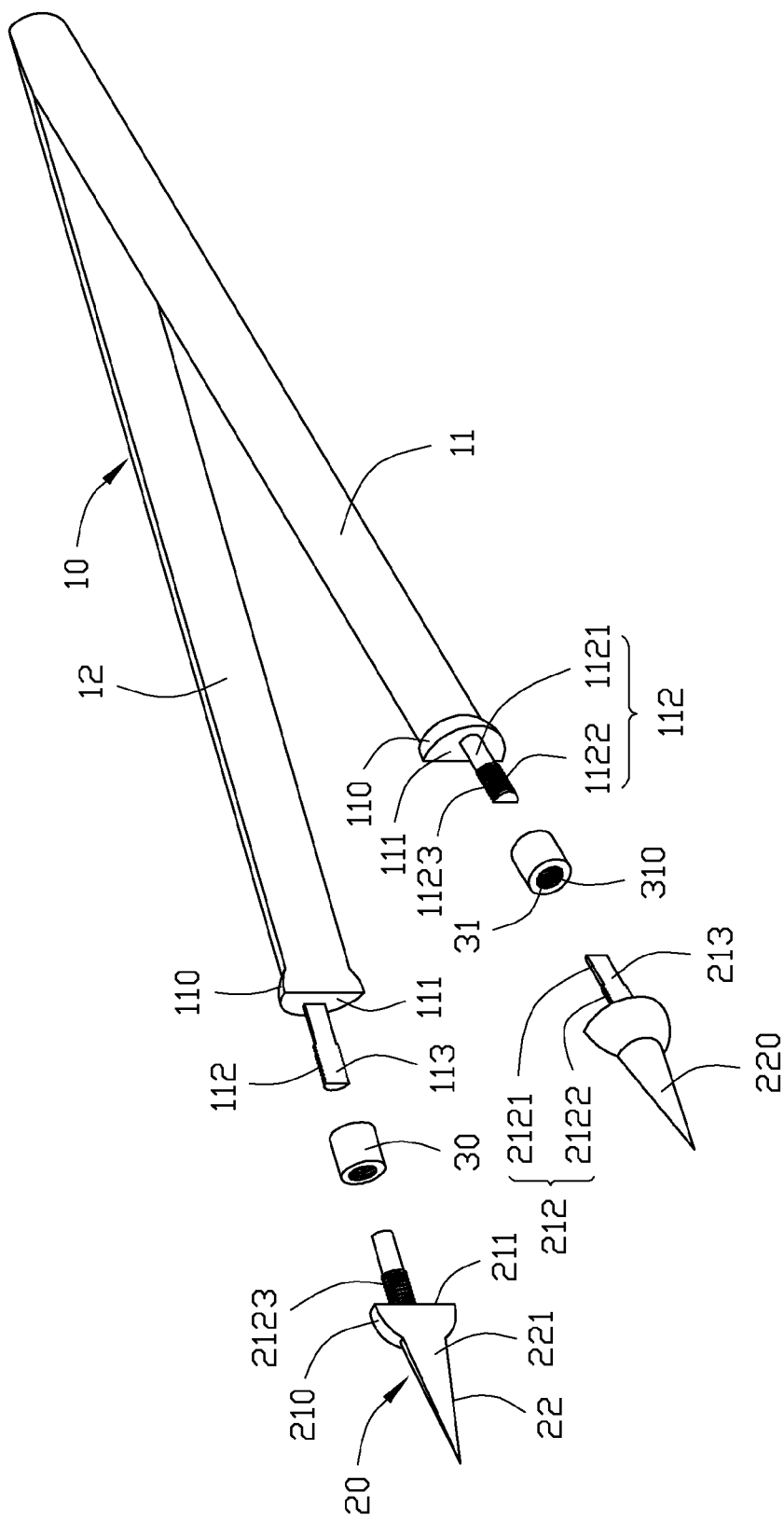
FIG. 2 is an exploded view of the forceps of FIG. 1.

Referring to FIG. 2, each of the two arms 10 is strip-shaped and resilient. The two arms 10 are arranged in V-shape with top ends thereof joined together and bottom ends thereof spaced from each other. Each of the two arms 10 includes a semi-circular outer surface 11 and a planar inner surface 12 opposite to the outer surface 11. The inner surfaces 12 of the two arms 10 face each other.

The outer surface 11 of each of the arms 10 expands gradually at the bottom end thereof to form a first mounting portion 110. The first mounting portion 110 has a truncated semiconic shape with a first mounting surface 111 provided at a bottom thereof. The first mounting surface 111 of each arm 10 is perpendicular to the inner surface 12 of the arm 10. An area of the first mounting surface 111 is larger than that of a cross section of the arm 10. A first mounting pole 112 extends downwardly and perpendicularly from a middle portion of each first mounting surface 111 along a lengthwise direction of the arm 10. The first mounting pole 112 is semi-cylindrical with a planar joint surface 113 provided at an inner side thereof. The joint surfaces 113 of the two first mounting poles 112 face each other. Each of the joint surfaces 113 is parallel to the inner surface 12 of a corresponding arm 10. The first mounting pole 112 includes a smooth section 1121 adjacent to the first mounting portion 110 and a thread section 1122 away from the first mounting portion 110. The smooth section 1121 and the thread section 1122 each are semi-cylindrical. The diameter of the smooth section 1121 is a little smaller than that of the thread section 1122. The thread section 1122 defines a plurality of threads 1123 in a semi-circular outer surface thereof which is opposite to the joint surface 113 of the first mounting pole 112, wherein the threads 1123 are defined substantially along a circumferential direction of the semi-circular outer surface of the thread section 1122.

Figure 3:
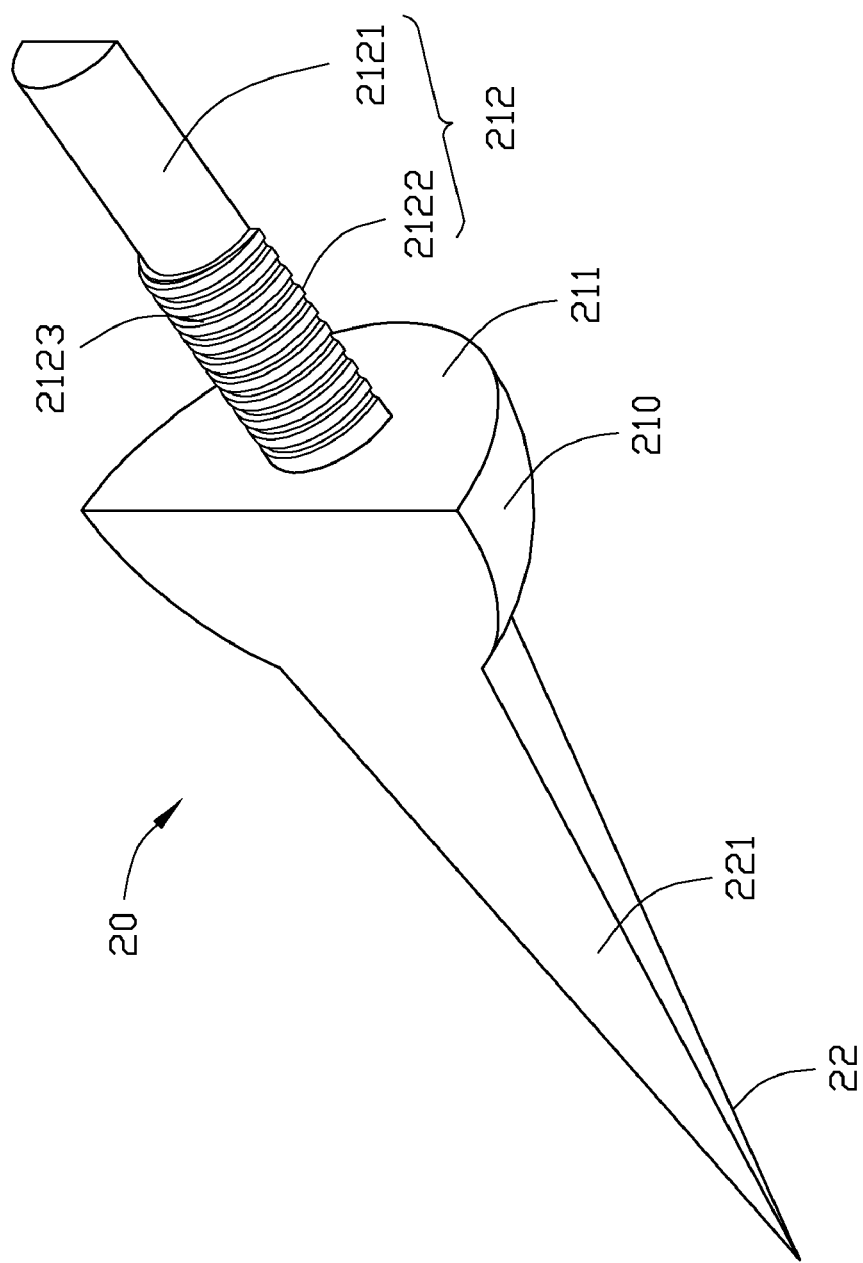
FIG. 3 is an enlarged view of a nipping tip of the forceps of FIG. 2.

The two nipping tips 20 are identical to each other. Referring also to FIG. 3, each of the nipping tips 20 includes a semiconic nipping portion 22. The nipping portion 22 includes an outer surface 220 and an inner nipping surface 221. The nipping surfaces 221 of the two nipping tips 20 face each other. Each of the nipping tips 20 expands outwardly to form a second mounting portion 210 at a top end thereof. The second mounting portion 210 has a truncated semiconic shape with a second mounting surface 211 formed at a top thereof. The second mounting surface 211 of each nipping tip 20 is perpendicular to the nipping surface 221 of the nipping tip 20. An area of the second mounting surface 211 is larger than that of a cross section of the top end of the nipping portion 22. A second mounting pole 212 extends upwardly and perpendicularly from a middle portion of each second mounting surface 211 along a lengthwise direction of the nipping tip 20. The second mounting pole 212 is semi-cylindrical with a planar joint surface 213 (referring to FIG. 2) provided at an outer side thereof. The joint surface 213 is parallel to the nipping surface 221 of the nipping tip 20, and the joint surface 213 and the nipping surface 221 of the nipping tip 20 face two opposite directions. The second mounting pole 212 includes a thread section 2122 adjacent to the second mounting portion 210 and a smooth section 2121 away from the second mounting portion 210. The smooth section 2121 and the thread section 2122 each are semi-cylindrical. The diameter of the smooth section 2121 is a little smaller than that of the thread section 2122. The thread section 2122 defines a plurality of threads 2123 in a semicircular outer surface thereof which is opposite to the joint surface 213 of the second mounting pole 212, wherein the threads 2123 are defined substantially along a circumferential direction of the semicircular outer surface of the thread section 2122.

Referring to FIG. 2, the sleeves 30 are substantially tubular. Each of the sleeves 30 defines a through hole 31 therein, and forms a plurality of threads 310 on an inner surface thereof around the through hole 31.

Figure 4:
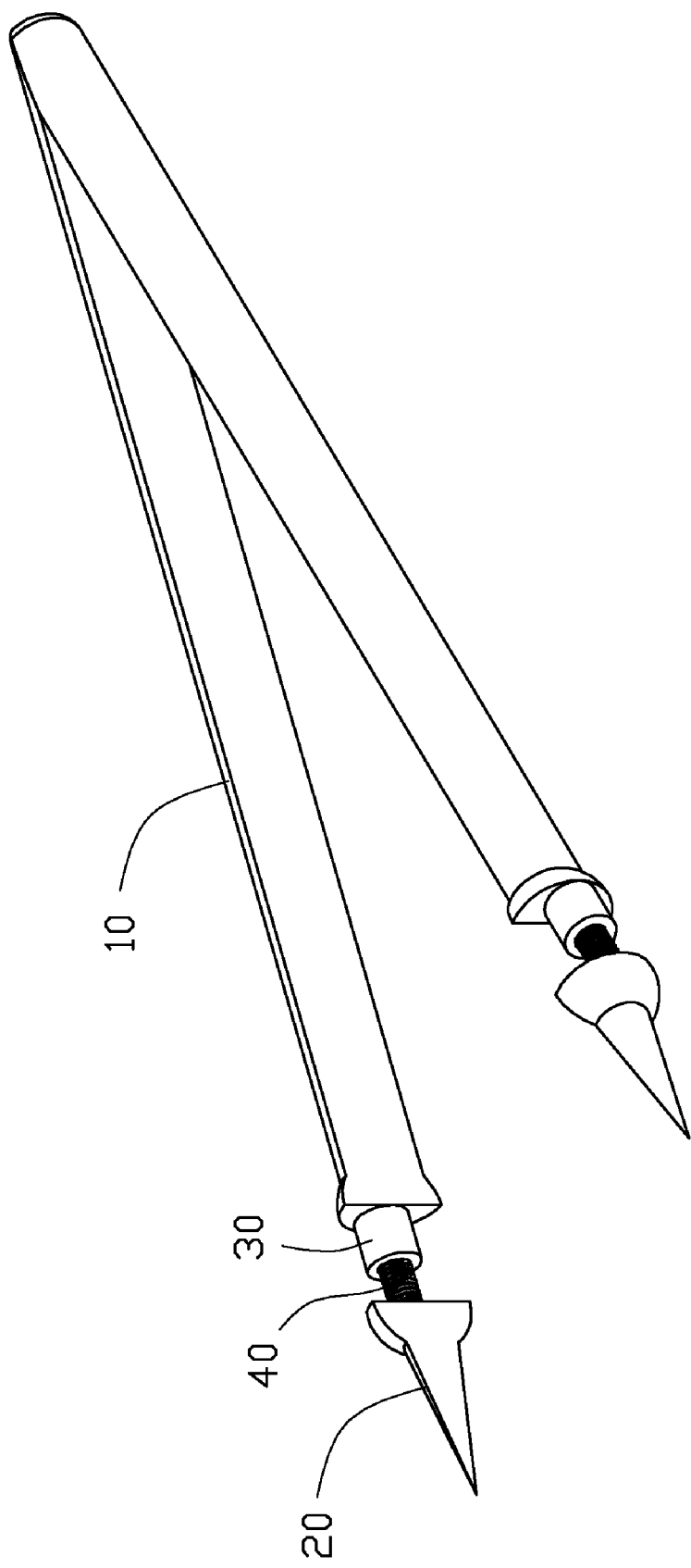
FIG. 4 is a preassembled view of the forceps of FIG. 2.

In assembly, each sleeve 30 is threaded onto a corresponding first mounting pole 112 from the thread section 1122 thereof, until the sleeve 30 is loosely placed around the smooth section 1121 thereof. The second mounting pole 212 of each nipping tip 20 is inserted into the through hole 31 of a corresponding sleeve 30 until a free end of the smooth section 2121 of the second mounting pole 212 abuts against the first mounting surface 111 of a corresponding arm 10, and a free end of the thread section 1122 of the first mounting pole 112 abuts against the second mounting surface 211 of a corresponding nipping tip 20. In this state, the joint surface 113 of the first mounting pole 112 abuts against the joint surface 213 of a corresponding second mounting pole 212, the thread sections 1122, 2122 of the first mounting pole 112 and the corresponding second mounting pole 212 cooperatively form a thread pole 40 (referring to FIG. 4), and the smooth sections 1121, 2121 of the first mounting pole 112 and the corresponding second mounting pole 212 cooperatively form a smooth pole 50 (referring to FIG. 1). An diameter of the thread pole 40 is a little larger than that of the smooth pole 50 and equal to that of the through hole 31 of the sleeve 30, and the sleeve 30 is loosely placed around the smooth pole 50. Then, the sleeve 30 is threaded from the smooth pole 50 to the thread pole 40 until the sleeve 30 abuts against the second mounting surface 211 of the corresponding nipping tip 20. Until now, the nipping tips 20 are securely mounted on the arms 10.

When the nipping tips 20 of the forceps are damaged, the damaged nipping tips 20 can be replaced with new ones. Therefore, the forceps is reusable and resources are greatly economized. In addition, the nipping tips 20 are detachably mounted on the arms 10 of the forceps, whereby the forceps can be replaced with different nipping tips 20 for different uses.

It is to be understood, however, that even though numerous characteristics and advantages of the present invention have been set forth in the foregoing description, together with details of the structure and function of the embodiments, the disclosure is illustrative only, and changes may be made in detail, especially in matters of shape, size, and arrangement of parts within the principles of the invention to the full extent indicated by the broad general meaning of the terms in which the appended claims are expressed.

What is claimed is:

1. A forceps, comprising:

two arms with top ends thereof being joined together and bottom ends thereof being spaced from each other; and two nipping tips respectively mounted on the bottom ends of the two arms by two sleeves, each of the sleeves defining a through hole therein and forming a plurality of threads on an inner surface thereof around the through hole for mounting a corresponding nipping tip;

wherein each of the two arms forms a first mounting pole extending from the bottom end thereof towards a corresponding nipping tip, each of the nipping tips forms a second mounting pole extending towards a corresponding arm, the first and second mounting poles each comprise a thread section and a smooth section at two opposite ends thereof, the first mounting pole of an arm and the second mounting pole of a corresponding nipping tip abut against each other and are received in the through hole of a corresponding sleeve, the thread section of the first mounting pole and the thread section of the second mounting pole cooperatively form a thread pole, the smooth section of the first mounting pole and the smooth section of the second mounting pole cooperatively form a smooth pole, the sleeve is threaded with the thread pole, whereby the two nipping tips are respectively mounted on the bottom ends of the two arms by the two sleeves.

2. The forceps of claim 1, wherein the smooth section of the first mounting pole is located adjacent to the bottom end of the arm, the thread section of the first mounting pole is located away from the bottom end of the arm, the thread section of the second mounting pole is located adjacent to the nipping tip, the smooth section of the second mounting pole is located away from the nipping tip.

3. The forceps of claim 1, wherein the first and second mounting poles each are semi-cylindrical and are provided with a planar joint surface, the joint surfaces of the first and second mounting poles abut against each other.

4. The forceps of claim 1, wherein each of the arms comprises a semi-circular outer surface and a planar inner surface, the inner surfaces of the two arms face each other.

5. The forceps of claim 1, wherein each of the nipping tips comprises a nipping portion, the nipping portion comprises an outer surface and a planar inner nipping surface, the nipping surfaces of the two nipping tips face each other.

6. The forceps of claim 1, wherein the bottom end of each of the arms expands downwardly to form a first mounting portion thereat, and the first mounting pole extends downwardly from the first mounting portion, the nipping tip expands upwardly at a top end thereof to form a second mounting portion thereat, and the second mounting pole extends upwardly from the second mounting portion.

7. The forceps of claim 6, wherein a first mounting surface is formed at a bottom of the first mounting portion, and the first mounting pole extends downwardly from the first mounting surface, a second mounting surface is formed at a top of the second mounting portion, and the second mounting pole extends upwardly from the second mounting surface.

8. The forceps of claim 7, wherein a free end of the first mounting pole abuts against the second mounting surface of the second mounting portion, a free end of the second mounting pole abuts against the first mounting surface of the first mounting portion.

* * * * *